United States Patent [19]

Belli Dell'Amico et al.

[11] Patent Number: 5,198,565
[45] Date of Patent: Mar. 30, 1993

[54] SILICON AND ALUMINUM N,N-DIALKYLCARBAMATES AND THEIR HYDROLYSIS PRODUCTS AND PROCESS FOR THEIR PREPARATION

[75] Inventors: Daniela Belli Dell'Amico, Pisa; Fausto Calderazzo, Ghezzano; Michela Dell'Innocenti, Calci; Pierluigi Robino, Asciano, all of Italy

[73] Assignee: Consiglio Nazionale Delle Ricerche, Rome, Italy

[21] Appl. No.: 766,113

[22] Filed: Sep. 27, 1991

Related U.S. Application Data

[63] Continuation-in-part of Ser. No. 500,997, Mar. 29, 1990, abandoned.

[30] Foreign Application Priority Data

Apr. 27, 1989 [IT] Italy ............................... 20284 A/89

[51] Int. Cl.$^5$ ................................................ C07F 7/10
[52] U.S. Cl. .................................... 556/420; 556/183
[58] Field of Search .................... 556/420, 183

[56] References Cited

U.S. PATENT DOCUMENTS

| | | | |
|---|---|---|---|
| 2,052,138 | 8/1936 | Hopff et al. | 556/183 |
| 3,056,820 | 10/1962 | Martinek | 556/183 X |
| 3,284,485 | 11/1966 | Goossens | 556/420 X |
| 4,400,526 | 8/1983 | Kanner et al. | 556/420 |
| 4,631,346 | 12/1986 | Webb et al. | 556/420 |
| 4,831,173 | 5/1989 | Knausz et al. | 556/420 |
| 4,837,349 | 6/1989 | Ohfune et al. | 556/420 |

*Primary Examiner*—Arthur C. Prescott
*Attorney, Agent, or Firm*—Birch, Stewart, Kolasch & Birch

[57] ABSTRACT

Silicon and aluminum N,N-dialkylcarbamates are prepared by reacting a secondary amine and $CO_2$ with respectively a silicon and an aluminum halide in a reaction medium consisting of an organic solvent and then hydrolyzed by treatment with water in an anhydrous organic solvent.

8 Claims, No Drawings

SILICON AND ALUMINUM N,N-DIALKYLCARBAMATES AND THEIR HYDROLYSIS PRODUCTS AND PROCESS FOR THEIR PREPARATION

This application is a continuation-in-part of application Ser. No. 07/500,997 filed on Mar. 29, 1990 now abandoned.

FIELD OF THE INVENTION

The present invention relates to silicon and aluminium organic derivatives and a process for their preparation.

SUMMARY OF THE INVENTION

This invention relates to new organic silicon and aluminium compounds, namely N,N-dialkylcarbamates of general formula (I):

$$M[O_2CNR_2]_n \quad (I)$$

where M is Si or Al, n is 4 when M is Si and 3 when M is Al, and R is a $C_4$-$C_6$ alkyl group.

The invention also relates to the hydrolysis products of the compounds (I) and to the process for preparing the compounds (I) and their hydrolysis products.

The process for preparing the compounds (I) and their hydrolysis products is characterised by:
a) reacting a secondary amine and $CO_2$ with an $MX_n$ halide in which M is Si or Al, X is Cl or Br, and n is 4 when M is Si and 3 when M is Al, in a reaction medium consisting of an organic solvent;
b) filtering off the dialkylammonium chloride which forms;
c) precipitating the compound (I) by concentrating the filtered solution, and if necessary cooling and adding n-heptane;
d) recovering the product (I) by filtration;
e) dissolving the product (I) in an organic solvent and hydrolyzing with water; and
f) recovering the hydrolysis product by filtration.

DETAILED DESCRIPTION OF THE INVENTION

The characteristics and advantages of the silicon and aluminium N,N-dialkyl-carbamates of formula (I) and their hydrolysis products, and the process for preparing the compounds (I) and their hydrolysis products will be more apparent from the following detailed description.

The compounds of formula (I) are prepared by reacting a secondary amine and $CO_2$ with an $MX_n$ halide as heretofore defined.

To effect this reaction, a solution of $MX_n$ in an organic solvent is gradually added to a solution of $R_2NH$ and $CO_2$ in an organic solvent. The organic solvent is chosen from the group comprising saturated aliphatic and aromatic hydrocarbons and is preferably toluene.

The organic solvent has a water content of less than 50 ppm.

The concentration of the secondary amine solution is between 0.5 and 5 moles/l and the concentration of the $MX_n$ solution is between 0.1 and 2 moles/l.

The molar ratio of secondary amine to $MX_n$ used in the reaction is between 8 and 12.

The $MX_n$ solution is added to the secondary amine solution under a $CO_2$ atmosphere.

When the addition is complete the reaction mixture is kept stirring at a temperature of between 15° C. and 30° C. under a $CO_2$ atmosphere for a time of between 4 and 8 hours.

On termination of the reaction the mixture consists of a colourless solution of (I) and a colourless solid consisting of dialkylammonium chloride.

The reaction mixture is filtered and the solution recovered.

To recover (I) when M is Si, the solution is concentrated by evaporating the solvent at ambient temperature under reduced pressure, until a concentration of (I) of between 1 and 2 moles/l is obtained, then cooling to −30° C. and adding n-heptane in a quantity of between 1 and 3 volume of solution while maintaining the temperature at −30° C.

The product (I) in which M is Si thus precipitates, and is separated by filtration under a $CO_2$ atmosphere.

To recover (I) when M is Al, the solution is evaporated to dryness under reduced pressure, the residue taken up in n-heptane and the product separated by filtration.

The compounds (I) are soluble in both aromatic and aliphatic hydrocarbons, and are very sensitive to atmospheric moisture, by which they hydrolyze rapidly.

The hydrolysis products of the compounds (I) find important use in the production of very pure zeolites, with the introduction of the cations of interest.

The hydrolysis of the compound (I) is carried out by dissolving said compound of formula (I) in an organic solvent, by adding $H_2O$ to the obtained solution and maintaining the mixture under stirring at at a temperature of from 15° to 40° C. for 0.5-2 hours.

Typically, the compound (I) is dissolved in the organic solvent, preferably under an atmosphere of dry argon, the quantities used being such as to obtain a concentration of (I) in said solvent which ranges from 0.05 to 2 moles/l; $H_2O$ is then added to the solution in such a quantity as to obtain a molar ratio of $H_2O$ to said compound (I) of between 2 and 60.

The hydrolysis product is a colorless solid which is recovered by filtration and dried at a reduced pressure, typically from 1 to 100 Pa, at a temperature below 100° C. for a time of from 2 to 12 hours.

The organic solvents suitable for the hydrolysis step are the aromatic or aliphatic hydrocarbons and the water miscible ethers, particularly tetrahydrofuran or dimethoxyethane.

According to one preferred embodiment of the present invention silicon oxides and/or dialkylammonium silicates of the general formula $(NH_2R_2)_2Si_nO_{2n+1}$, wherein n is a number comprised between 5 and 40 and R is a $C_1$-$C_6$ alkyl group, are produced by hydrolyzing the N,N-dialkylcarbamates of silicon of the general formula $Si(O_2CNR_2)_4$ optionally followed by the thermal decomposition of the obtained dialkylammonium silicates to silicon oxide.

The hydrolysis of silicon N,N-dialkylcarbamates of silicon is represented by the following equation (1):

$$Si(O_2CNR_2)_4 + (2n+1)H_2O \xrightarrow{n} (NH_2R_2)_2Si_nO_{2n+1} + (4n-2)R_2NH + 4n\,CO_2$$

The hydrolysis is carried out normally in an organic solvent, in which the starting silicon compound is soluble, namely in an aliphatic or aromatic hydrocarbon, a water-miscible ether such as tetrahydrofuran or dimethoxyethane at a temperature of from 15° to 40° C. or lower, the resultant solid is normally collected by filtration, washed with an organic liquid, or with water, dried in vacuo at at a temperature of from 15° to 40° C. or higher and, if required by the further use, treated thermally at temperatures comprised between 100° and 600° C., to give $SiO_2$, according to equation (2).

The silica thus produced has a high surface area, it is normally amorphous and finds practical use as a support of high chemical purity.

As a matter of fact, the advantageous metal content of the solid obtained by hydrolysis is as low as that of $SiCl_4$, an easily purified liquid, which, according to the above specified applications is the starting material for the preparation of the N,N-dialkylcarbamate precursors.

$$(NH_2R_2)_2Si_nO_{2n+1} \xrightarrow{heat} n\ SiO_2 + 2\ NHR_2 + H_2O \qquad (2)$$

The production of silica or dialkylammonium silicates by the method of the present invention has several advantages with respect to the alternative routes of the prior art, mainly hydrolysis of $SiCl_4$ or $Si(OR)_4$. As the hydrolysis is extremely fast even at room temperature, the precipitate obtained by the present method is highly dispersed and amorphous. On the other hand, due to the ionic nature of the products, the solid particles easily precipitate; accordingly, no particular difficulty is encountered in the filtration stage. Moreover, as carbon dioxide is evolved, the hydrolysis of equation 1 is a thermodynamically favourable process and no products of partial hydrolysis are observed and equilibria involving partially converted products are not encountered. A further advantage is the absence of the noxious and corrosive HCl, the latter being converted to $R_2NH.HCl$ during the preparation of the silicon carbamate precursors. The amine can be easily removed from the dialkylammonium chloride in the presence of a base and recycled for the synthesis of $Si(O_2CNR_2)_4$.

The isolation of the $Si(O_2CNR_2)_4$ to produce silicon oxide is not required, in the preparation of the hydrolytic products. As specified in one of the examples, the crude solution obtained from the $SiCl_4/CO_2/R_2NH$ system, after removal of $R_2NH.HCl$ and of the excess amine by evaporation under reduced pressure, can be treated with water. If this preparative procedure is adopted, the preparation of the $Si(O_2CNR_2)_4$ precursor is best carried out in a water-miscible inert organic solvent.

The following examples of the preparation of the compounds according to the invention are given by way of non-limiting illustration.

EXAMPLE 1

$SiCl_4$ (5 ml; 0.043 moles) dissolved in anhydrous toluene (100 ml) is added slowly under a carbon dioxide atmosphere to a solution of 35.5 g (0.485 moles) of diethylamine $NHEt_2$ in anhydrous toluene (200 ml). After stirring for 5 hours at a temperature of 23° C. in a $CO_2$ atmosphere, the reaction mixture comprised a colourless solution and a colourless solid consisting of diethylammonium chloride. The reaction mixture was filtered under $CO_2$ and the solution was recovered, for which the chloride test was found negative, and was concentrated under reduced pressure ($10^{-2}$ Torr) to a volume of 30 ml, and cooled to about $-30°$ C.

This treatment resulted in the partial crystallization of the silicon N,N-diethylcarbamate, which was recovered as a colourless solid by filtration and dried at 20° C. under reduced pressure to obtain 5.7 g of product. After cooling the toluene solution, resulting from the filtration, to about $-30°$ C. and adding 30 ml of n-heptane, a further 12.45 g of product were recovered, to give an overall yield of 86% on the silicon tetrachloride used.

The product was analyzed for silicon content by combustion and for carbon dioxide content by decomposing with 20% sulphuric acid and measuring the volume of the gas evolved. Analysis: % found (calculated values for $C_{20}H_{40}N_4O_8Si$ being given in parentheses): Si, 5.7 (5.7); $CO_2$, 32.9 (35.7). The compound has an intense IR band at 1710 $cm^{-1}$ due to the coordinated carbamate grouping. The $^1H$-NMR spectrum shows two resonances corresponding to absorption of the methylene and methyl groups bonded to the nitrogen of the carbamate group, $Si[O_2CN(CH_2CH_3)_2]_4$.

The silicon N,N-diethylcarbamate, $Si(O_2CNEt_2)_4$, obtained (2.47 g; 5.01 mmol) was dissolved in tetrahydrofuran (100 ml) under a nitrogen atmosphere and treated with 0.36 g (20.0 mmol) of $H_2O$ (molar ratio $H_2O/Si=4$) at room temperature. The colorless suspension thus obtained was stirred for 1 h and then filtered. The finely divided colorless solid was dried for 12 h under reduced pressure (about $10^{-2}$ Torr) at room temperature (0.401 g, corresponding to a 90% yield based on the silicon content of the product).

Analysis: found % (calculated values in parenthesis for the formulation $[NH_2(C_2H_5)_2]_2Si_9O_{19}.2H_2O.0.5C_4H_8O$; $C_{10}H_{32}N_2O_{21.5}Si_{19}$): C=14.2(15.5); H=3.8(4.1); N=3.3(3.6); Si=31.7(32.5).

EXAMPLE 2

Example 1 is repeated, using diisopropylamine in place of the diethylamine.

Silicon N,N-diisopropylcarbamate, $Si[O_2CNPr_2]_4$, was obtained and was analyzed for its silicon and carbon dioxide content as indicated in Example 1. Analysis: % found (calculated values for $C_{28}H_{56}N_4O_8Si$ being given in parentheses): Si, 4.2 (4.6); $CO_2$, 26.8 (29.1). $CO_2$:Si molar ratio=4.1.

The silicon diisopropylcarbamate ($Si(O_2CNR_2)_4$, prepared (3.6 g; 5.95 mmol) dissolved in tetrahydrofuran (200 ml) was treated with water (6.0 g; 333 mmol; $N_2O/Si$ molar ratio=56) at room temperature. The colorless precipitate (0.32 g) was collected by filtration and dried at room temperature under reduced pressured (70% yield on the basis of the analytical silicon content).

Analysis found % (calculated values in parenthesis for the formulation $[NH_2(C_3H_7)_2]_2Si_{20}O_{41}.C_4H_8O$; $C_{16}H_{40}N_2O_{42}Si_{20}$): C=12.6 (12.9); H=2.9(2.7); N=1.8(1.9); Si=36.6(37.6).

A X-ray powder diagram showed the substance to be amorphous.

EXAMPLE 3

The silicon N,N-diethylcarbamate, $Si[O_2CNEt_2]_4$, obtained in Example 1 (2.47 g; 5.01 mmoles) was dissolved in anhydrous tetrahydrofuran (100 ml) under a dry argon atmosphere and treated with 0.36 g (20.0 mmoles) of $H_2O$ at ambient temperature. A colourless suspension immediately formed and was kept stirring for 1 hour after which it was filtered under argon. The resultant finely divided colourless solid was dried for 12 hours under reduced pressure (about $10^{-2}$ Torr) at ambient temperature. 0.401 g were obtained with a yield of 90.3% based on the silicon content of the product.

Analysis: % found (calculated values for [NH$_2$(C$_2$H$_5$)$_2$]$_2$Si$_8$O$_{17}$.3H$_2$O, C$_8$H$_{30}$N$_2$O$_{20}$Si$_8$ given in parentheses): C, 14,2; 12.9 (13.7); H, 3.8; 3.6 (4.3); N, 3.1; 3.3 (4.0); Si, 31.7 (32.1).

EXAMPLE 4

Example 3 was repeated using a H$_2$O:Si molar ratio of 2.

A finely divided colourless product was obtained, of appearance similar to the product of Example 3.

The product had the following analytical composition: C, 15.0%; H, 4.2%; N, 4.0%.

EXAMPLE 5

30 ml (21.66 g; 214 mmoles) of NH(iC$_3$H$_7$)$_2$ are dissolved in 200 ml of anhydrous toluene at atmospheric pressure under carbon dioxide. 5.05 g of AlBr$_3$ (18.9 mmoles) are then added and the resultant suspension is stirred at ambient temperature for 7 hours. After filtering off the di-isopropylammonium hydrobromide which forms, the carbamate solution is evaporated to dryness under reduced pressure. The residue is taken up in n-heptane (30 ml), the resultant suspension is filtered and the aluminium dialkylcarbamate which collects on the filter is dried under a mechanical pump (ca. $10^{-1}$ mmHg) for 2 hours. 4.3 g of product are obtained with a yield of 49.5%. The colourless microcrystalline product has good solubility in aromatic hydrocarbon solvents, moderate solubility in saturated hydrocarbon solvents and good solubility in CCl$_4$.

Elemental analysis: found % (calculated values for Al[O$_2$CN(C$_3$H$_7$)$_2$]$_3$, C$_{21}$H$_{42}$AlN$_3$O$_6$ given in parentheses): C, 53.0 (54.9); H, 8.9 (9.2); Al, 6.0 (5.9); CO$_2$, 27.3 (28.7); N, 8.4 (9.1). The product is very sensitive to atmospheric moisture. The infrared band (in polychlorotrifluoroethylene) shows absorption bands at 2960, 2930, 2880, 1620, 1550 f, 1500 f.

EXAMPLE 6

A reaction flask of 4 liter capacity was charged with 60 ml (d=1.483; 88.98 g; 524 mmol) of SiCl$_4$, 2 l of toluene and 0.8 l of di-iso-propylamine (d=0.722; 577.6 g; 5.71 mol). After admission of CO$_2$ at atmospheric pressure, the resulting suspension was stirred for 12 h and finally filtered to eliminate the substantially insoluble C$_3$H$_7$NH.HCl. The toluene solution was evaporated to dryness under reduced pressure and the resulting solid residue of Si(O$_2$CN-isoPr$_2$)$_4$ was dissolved in tetrahydrofuran (750 ml) and treated at room temperature with a solution of H$_2$O (50 g; 2.77 mol, H$_2$O/Si molar ratio=5.3) in 200 of tetrahydrofuran. Carbon dioxide was evolved and the resulting suspension was stirred for 12 h and then filtered. The solid was dried at room temperature under reduced pressure (136 g, with a silicon content of 8.8%, corresponding to a 81% yield with respect to the SiCl$_4$ introduced). The thermogravimetric analysis of this product showed an ultimate weight loss of 81.9%. Most of the volatile products were lost at temperature $\leq 100°$ C., the process being complete at about 600° C. in air.

The reuslting SiO$_2$-containing product has a surface area of about 700 m$^2 \times$ g$^{-1}$, as determined by N$_2$ absorption at 77° K.

EXAMPLE 7

In a reaction flask of 1 liter capacity, silicon N,N-diisopropylcarbamate (39 g; 64.5 mmol) dissolved in dimethoxyethane (500 ml) was treated with H$_2$O (11.6 g; 0.64 mol; H$_2$O:Si molar ratio corresponding to 10) dissolved in dimethoxyethane (200 ml) at room temperature. The colorless precipitate was filtered off and dried in vacuo at room temperature. Further treatment of the solid under reduced pressure (about $10^{-2}$ Torr) at 120° C. gave a solid with the following analytical data:

Analysis: found % (calculated values in parenthesis for the formulation [NH$_2$(C$_3$H$_7$)$_2$]$_2$Si$_{28}$O$_{57}$.C$_4$H$_{10}$O$_2$.-H$_2$O; C$_{16}$H$_{44}$N$_2$O$_{60}$Si$_{28}$): C=9.8(9.6); H=2.6(2.2); N=1.4(1.4); Si=39.4(39.1).

EXAMPLE 8

Silicon N,N diisopropylcarbamate (280 g; 0.46 mol) dissolved in tetrahydrofuran (600 ml) was treated at room temperature with H$_2$O (50 g; 2.77 mol; H$_2$O/Si molar ratio=6) dissolved in 200 ml of tetrahydrofuran. After work-up similar to that of Example 7, the colorless solid, after filtration, was washed with water and then dried in vacuo at room temperature for 10 h. The resulting solid gave the following analytical results:

Analysis: found % (calculated values in parenthesis for the formulation [NH$_2$(C$_3$H$_7$)$_2$]$_2$Si$_{25}$O$_{51}$.0.5C$_4$H$_8$O.6-H$_2$O; C$_{14}$H$_{48}$N$_2$O$_{57.5}$Si$_{25}$): c, 9.2(9.0); H, 2.7(2.6); N, 1.5(1.5); Si, 38.3(37.6).

We claim:

1. A process for hydrolyzing a N,N-dialkylcarbamate of the general formula (I):

$$M[O_2CNR_2]_n \qquad (I)$$

wherein M is Si or Al; n is 4 when M is Si and 3 when M is Al; R is a C$_1$-C$_6$ alkyl group comprising a) dissolving said compound of formula (I) in an organic solvent up to a concentration of from 0.05 to 2 moles/l, b) adding H$_2$O to the obtained solution in such a quantity as to obtain a molar ratio of H$_2$O to said product (I) of between 2 and 60 and running the hydrolysis at a temperature of from 15° to 40° C. for 0.5–2 hours, under stirring; and c) recovering the hydrolysis product by filtration and drying it at a reduced pressure at a temperature below 100° C. for a time of from 2 to 12 hours.

2. The process as claimed in 1, wherein said organic solvent is selected in the group consisting of aromatic and aliphatic hydrocarbons, and water miscible ethers.

3. The process as claimed in claim 2, wherein said solvent is tetrahydrofuran.

4. The process as claimed in claim 2, wherein said solvent is dimethoxyethane.

5. A process for hydrolyzing a N,N-dialkylcarbamate of the general formula (I):

$$M[O_2CNR_2]_n \qquad (I)$$

wherein M is Si; n is 4; R is a C$_1$-C$_6$ alkyl group comprising a) dissolving said compound of formula (I) in an organic solvent up to a concentration of from 0.05 to 2 moles/l, b) adding H$_2$O to the obtained solution in such a quantity as to obtain a molar ratio of H$_2$O to said product (I) of between 2 and 60 and running the hydrolysis at a temperature of from 15° to 40° C. for 0.5–2 hours, under stirring; and c) recovering the hydrolysis product by filtration and drying it at a reduced pressure at a temperature below 100° C. for a time of from 2 to 12 hours, and optionally decomposing said obtained hydrolysis product by thermal treating at a temperature of from 150° to 600° C. and recovering pure, solid, amorphous $SiO_2$ having a high surface area.

6. The process as claimed in claim 5, wherein said solvent is tetrahydrofuran.

7. The process as claimed in claim 5, wherein said solvent is dimethoxyethane.

8. A process for hydrolyzing a N,N-dialkylcarbamate of the general formula (I):

$$M[O_2CNR_2]_n \qquad (I)$$

wherein M is Si; n is 4; R is a $C_1$–$C_6$ alkyl group comprising a) preparing said compound of formula (I) by reacting a secondary amine and $CO_2$ with $SiX_4$, wherein X is Cl of Br, in an anhydrous solvent selected from the group consisting of tetrahydrofuran and dimethoxyethane, at a temperature of from 15° to 30° C., in a $CO_2$ atmosphere, for a period of time of between 4 and 8 hours, said secondary amine and $SiX_4$ being in a molar ratio of from 8 to 12;

b) filtering off dialkylammonium halide which forms as a result of said reaction (a);

c) adding $H_2O$ to the filtered solution in such a quantity as to obtain a molar ratio of $H_2O$ to said product (I) of between 2 and 60 and running the hydrolysis at a temperature of from 15° to 40° C. for 0.5–2 hours, under stirring; and d) recovering the hydrolysis product by filtration and drying it at a reduced pressure at a temperature below 100° C. for a time of from 2 to 12 hours, and optionally decomposing said obtained hydrolysis product by thermal treating at a temperature of from 150° to 600° C. and recovering pure, solid, amorphous $SiO_2$ having a high surface area.

* * * * *